(12) United States Patent
Zhang et al.

(10) Patent No.: US 9,283,416 B2
(45) Date of Patent: Mar. 15, 2016

(54) STAR-SHAPED HYPERBRANCHED POLYMER WITH TRIETHANOLAMINE CORE, CARBOXYLATE LATERAL GROUP AND DITHIOCARBOXYLATE END GROUP, AND PREPARING METHOD AS WELL AS APPLICATION THEREOF

(71) Applicant: Tongji University, Shanghai (CN)

(72) Inventors: Bingru Zhang, Shanghai (CN); Fengting Li, Shanghai (CN); Zhipeng Tian, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 14/681,051

(22) Filed: Apr. 7, 2015

(65) Prior Publication Data

US 2015/0283417 A1    Oct. 8, 2015

(30) Foreign Application Priority Data

Apr. 8, 2014    (CN) .......................... 2014 1 0137960

(51) Int. Cl.
| | |
|---|---|
| *A62D 3/33* | (2007.01) |
| *C07C 213/06* | (2006.01) |
| *C07C 213/08* | (2006.01) |
| *C07C 227/06* | (2006.01) |
| *C07C 333/20* | (2006.01) |
| *C07C 333/16* | (2006.01) |
| *A62D 101/08* | (2007.01) |

(52) U.S. Cl.
CPC ................ *A62D 3/33* (2013.01); *C07C 213/06* (2013.01); *C07C 213/08* (2013.01); *C07C 227/06* (2013.01); *C07C 333/16* (2013.01); *C07C 333/20* (2013.01); *A62D 2101/08* (2013.01)

(58) Field of Classification Search
CPC ........................................................ A62D 3/33
USPC .......................................................... 588/315
See application file for complete search history.

(56) References Cited

U.S. PATENT DOCUMENTS 8,975,340 B2 *  3/2015  Yengoyan ................ B01J 39/04
                                                        525/328.4

* cited by examiner

*Primary Examiner* — Edward Johnson

(57) ABSTRACT

A star-shaped hyperbranched polymer with a triethanolamine core, a carboxylate lateral group and a dithiocarboxylate end group has a formula of $N[CH_2CH_2OCOCH_2CH_2(COOM)N(CSSM)CH_2CH_2N(CSSM)_2]_3$, wherein M is $Na^+$, $NH_4^+$ or $K^+$. The star-shaped hyperbranched polymer has an effectively stabilization effect on heavy metals in MSWI fly ash. A method thereof for stabilizing is simple, low in dosage, cheap and without secondary pollution. Therefore, heavy metals leaching concentration in fly ash stabilized production is lower than a limit of Chinese national standard. Furthermore, acid and alkali resistance thereof is sufficient, which decreases a long-term pollution risk in natural environment.

6 Claims, 4 Drawing Sheets

STAR-SHAPED HYPERBRANCHED POLYMER WITH TRIETHANOLAMINE CORE, CARBOXYLATE LATERAL GROUP AND DITHIOCARBOXYLATE END GROUP, AND PREPARING METHOD AS WELL AS APPLICATION THEREOF

CROSS REFERENCE OF RELATED APPLICATION

The present invention claims priority under 35 U.S.C. 119 (a-d) to CN 201410137960.2, filed Apr. 8, 2014.

BACKGROUND OF THE PRESENT INVENTION

1. Field of Invention

The present invention relates to a technical field of chemical and environmental protection, and more particular to a star-shaped hyperbranched polymer with a triethanolamine core, a carboxylate lateral group and a dithiocarboxylate end group, and a preparing method as well as application thereof for stabilizing heavy metals in MSWI (Municipal Solid Waste Incineration) fly ash.

2. Description of Related Arts

In recent years, "junk-besieged city" phenomenon is spreading around the world. Because waste incineration takes a small area, advantages such as waste reduction, harmlessness and recycling can be maximized. Waste incineration is becoming a generally adopted waste disposal technology in developed world countries, and also a major policy of Chinese government to deal with "junk-besieged city" phenomenon. With the increasing of "junk-besieged city" phenomenon, Chinese waste incineration scale is also increasing year by year, which had been increased from 3.699 million tons in 2003 to 35.84 million tons in 2012, sharing an increase of 969%. In 2015, waste incineration scale of China will reach 112.11 million tons (according to "twelfth five-year" national urban domestic waste treatment facilities construction plan, 2012).

However, after incineration, fly ash will be produced with an amount equivalent of 2%-5% of a junk weight. Fly ash has high leaching toxic heavy metals such as As, Cd, Cr, Hg and Pb which are listed as hazardous wastes in national standard Waste Incineration Landfill Pollution Control Standard (GB16889-2008), and cannot be directly land-filled. Fly ash must reach the control indicators of the above standard before landfill in a domestic waste landfill site.

Treatment of fly ash comprises: extraction method, heat treatment method, solidification/stabilization method, and chemical agent stabilization method. Extraction method uses water, acids, alkali, or other solvents for leaching heavy metals in fly ash. However, the heavy metals travel from a solid phase into a liquid phase, which raises a new problem of wastewater treatment, and is expensive. Heat treatment comprises: sintering, vitrification and melting, wherein the fly ash is respectively heated to 900-1000° C., 1100-1500° C., and more than 1200° C., and then cooled to form amorphous, crystalline, or homogeneous glassy products. Although, heat treatment can effectively stabilize the heavy metals, construction and operating costs are high, and energy consumption is great. Furthermore, high-temperature process will generate melted fly ash which is more toxic, comprising heavy metals with a higher concentration. The solidification/stabilization method requires chemical additives such as cement, sodium silicate and lime for stabilizing before solidified, wherein the most commonly applied method is cement solidification/stabilization due to low cost. However, weight of the original fly ash is significantly increased (nearly two times), and stabilizing ability thereof on heavy metals is insufficient. There is a possible long-term release. In case of rain, soluble salt will be bleeded; and in a long-term natural environment of acid rain, the heavy metals will be leached, resulting in soil re-contaminating.

The chemical agent stabilization method uses agents to react with toxic substances in fly ash, for converting the toxic substances to low solubility, low dissolution and low toxic substances. Compared with other stabilization techniques, chemical agent stabilization method can achieve waste harmlessness, while achieving less waste capacity or no waste capacity, so as to increase the overall efficiency and economy of hazardous waste treatment and disposal systems. The chemical agent stabilization method has been widespreadly concerned in developed countries because of low operating cost. Especially in Japan, incinerated fly ash is mainly chemical agent stabilized and land-filled.

Common chemical stabilizers are: (1) inorganic agents such as lime, phosphates, iron salts (ferrous salts and iron oxide), carbonates, sulfides (sodium thiosulfate and sodium sulfide), alumina, and sodium hydroxide; (2) organic agents such as thiourea, ethylene diamine tetraacetic acid (EDTA), salts of organic dithiocarbamate and dithiophosphate, organic phosphonates, and chitosan derivatives.

Chinese patent application 200510011651.1 discloses a method for stabilizing incinerated fly ash with soluble phosphate. Soluble phosphate comprises: phosphoric acid, sodium hydrogen phosphate, sodium dihydrogen phosphate, and trisodium phosphate, whose dosage is large during stabilizing fly ash, typically 3%-10% of the fly ash weight. Which phosphate should be used depends on pH of leached solution, wherein if pH>12, the sodium hydrogen phosphate, the sodium dihydrogen phosphate, or the trisodium phosphate is selected. However, stabilized product of $PO_4^{3-}$ is easily converted to $H_2PO_4^-$, $HPO_4^{2-}$ under pH of 5-9 (Grubb D. G., Guimaraes M. S. Valencia R., 2000. *Phosphate immobilization using all acidic type fly ash*. J. Hazard. Mater., 76(2):217-236), resulting in re-leaching of heavy metals. If pH<5, phosphate actually losses the stabilization effect on heavy metals. Therefore, PH value is the key factor in soluble phosphate stabilization. For the fly ash, no matter treated by Chinese HVEP (Horizontal Vibration Extraction Procedure) or America TPLC (Toxicity Characteristic Leaching Procedure), the pH value of the leached solution thereof is typically no less than 10, which assures the stabilization effect of phosphate on fly ash. In the long-term natural environment, acid rain will gradually neutralize alkaline substances in fly ash, in such a manner that the fly ash is in the external environment with pH<5, resulting in increasing of heavy metal leaching speed. Therefore, anti-acid ability of the phosphate-stabilized product of the fly ash is insufficient, which increases a long-term safety risk.

Sulfide, based on insoluble metal sulfide (MS) generated, stabilizes fly ash, thereby stabilizing heavy metals, wherein a dosage is typically 3%-10% of fly ash weight (Quina M. J., Bordado J. C. M., Quinta-Ferreira R. M., 2010. *Chemical stabilization of air pollution control residues from municipal solid waste incineration*. Hazard. Mater. 179(1-3):382-392). However, sulfides are similar to soluble phosphate, which means that heavy metals in fly ash can only be effectively stabilized under a certain pH range.

Similarly, inorganic salts such as iron salts, carbonates and hydroxides also have problems of large dosage and poor acid resistance.

Organic stabilizers are mainly: thiourea, ethylene diamine tetraacetic acid (EDTA), organic phosphonates, organic dithio carbamate, thiophosphate, etc.

Stabilization effect of thiourea on heavy metals in fly ash is significantly better than the one of inorganic sodium sulfide. When a dosage of thiourea is 0.7% of fly ash weight, Pb Leaching amount is below the Chinese national standard limit. However, for the same results, a dosage of sodium sulfide needs to be 5% (Zhao Y. C., Song L. J., Li G. J., 2002. *Chemical stabilization of MSW incinerator fly ashes*. J. Hazard. Mater. 95 (1-2): 47-63). Stabilizing effect of thiourea also depends on pH value. When leachate pH<8 (leaching agent pH=1), leaching speed of heavy metals is increased (Dan Chen, Guangren Qian, Houhu Zhang, Huajun Zhu, 2006. *Tea Saponin Stability and Change Solid Waste Incinerated Fly Ash Test* [J]. Journal of North University (Natural Science). 27 (6): 519-523).

Stabilization effect of ethylene diamine tetra-acetic acid (EDTA) on heavy metals is also dependent on pH value, wherein the pH must be more than 10 (Yuanyuan Liu, Li'ao Wang, Xiang Lin, Zhiqiang Cui, Yu Luo, Gang Hu, 2007. *Municipal Solid Waste Incineration Compatibility of heavy metals in fly ash stabilization experimental drug study* [J]. Journal of Environmental Engineering, 1 (10): 94-99). Therefore, EDTA acid resistance is also poor.

Chinese patent ZL 200410067071.X discloses a technology of stabilizing heavy metals in fly ash with organic phosphonates, wherein acid resistance thereof is also poor (Zhang, Houhu et al., *Organic acid HEDP stabilize heavy metals in waste incineration fly ash* [J]. Environmental pollution control technology and equipment, 2006, 7 (11): 45-48).

In recent years, a new type of fly ash stabilizer appears, whose chelation group is formed by dithiocarbamate (DTC) and two dithiophosphinylidyne (DTP). For example, Chinese patent application 200410090662.9 discloses a dithiocarbamate sodium fly ash stabilizer with polyethyleneimine as a basic skeleton; Chinese patent 200710190138.2 discloses a fly ash stabilizer combining dialkyl dithiophosphate compounds with flocculants; and Chinese patent application 200810032233.4 discloses a dialkyl dithiocarbamate fly ash stabilizer. These organic stabilizers all have good stabilizing effects on heavy metals.

Evaluation of the above inorganic and organic stabilizers is based on the old Chinese national standard *Hazardous Waste Identification Standard-Leaching Toxicity Identification* (GB5086.2-1997). With new Chinese national standard *Landfill implementation of pollution control standard* (GB16889-2008), requirements for fly ash stabilization are more strict. For example, the concentration limit of leached Pb is changed from 3 mg/L to 0.25 mg/L, and the concentration limit of leached Cd is changed from 0.3 mg/L to 0.15 mg/L. Dosages of the above inorganic and organic stabilizers need to be increased for satisfying new standard, resulting in great increase of cost. For example, when treating fly ash of a waste incineration site with sodium phosphate (Zhou, Bin et al., 2009), if the dosage is 10%, the Pb leaching concentration is 0.46 mg/L, meeting old standard (GB5086.2-1997) wherein a concentration limit is 3 mg/L. However, new standard (GB16889-2008) is not satisfied. Even if the dosage is 30%, the leached Pb concentration is 0.27 mg/L, still not meeting the new standard wherein a concentration limit is 0.25 mg/L. The new standard raises higher requirements for chemical stabilizers.

Therefore, for fly ash stabilizers research, a novel, efficient, and strong acid resistance stabilizer is badly needed. Conventional stabilizer limits must be exceeded and structure must be improved for increasing combining ability with heavy metals in fly ash, so as to obtain efficient, high acid resistance fly ash stabilizers.

With the development of polymer, based on the conventional one-dimensional linear, two-dimensional cross-linked or lightly branched polymer, highly branched polymer having a three-dimensional spatial structure is developed. According to structures, highly branched polymers are divided into dendritic polymers, hyperbranched polymers, star-shaped hyperbranched polymers, and star-shaped hybrid arm hyperbranched polymers. Dendritic polymers have a regular structure. Hyperbranched polymers have an irregular structure. Star-shaped polymers are hyperbranched polymers with no less than three branches connected by chemical bonds on the same central core, wherein chemical composition of each branch is identical, and molecular weight should be no difference. Star-shaped polymers have a three-dimensional snowflake-like structure, and are a special kind of highly branched polymers. And star-shaped hybrid arm hyperbranched polymers have at least one branched chain with different chemical composition or significant molecular weight difference.

Because of the special structure of the non-linear polymer, theoretical research value and industrial potential applications thereof have aroused widespread interest. In the $21^{st}$ century, the dendritic polymers have won more and more worldwide attention of scientists, and have important application prospect in fields of industry, agriculture, defense, biomedical, sustained-release materials, catalysis, etc.

According to the present invention, carboxylate and dithiocarboxylate are respectively grafted on a star-shaped hyperbranched polymer chain and an end group, so as to obtain a star-shaped hyperbranched polymer, wherein a structure thereof is novel in the world. The star-shaped hyperbranched polymers are good at stabilizing heavy metals in fly ash, and stabilized heavy metals have an excellent acid and alkali resistances, which ensures a long-term stability of fly ash in the environment.

SUMMARY OF THE PRESENT INVENTION

An object of the present invention is to overcome problems of inorganic stabilizers and most of organic stabilizers that dosage is large and acid resistance is insufficient, and to provide a polymer with sufficient stabilizing effect on heavy metals in fly ash, strong acid resistance and a novel structure, for lowering cost of stabilizing MSWI (Municipal Solid Waste Incineration) fly ash and satisfying a long-term safety requirement of fly ash treatment.

Accordingly, in order to accomplish the above object, the present invention provides a star-shaped hyperbranched polymer with a triethanolamine core, a carboxylate lateral group and a dithiocarboxylate end group, wherein a formula thereof is: $N[CH_2CH_2OCOCH_2CH_2(COOM)N(CSSM)CH_2CH_2N(CSSM)_2]_3$, wherein M is $Na^+$, $NH_4^+$ or $K^+$; a structural formula thereof is:

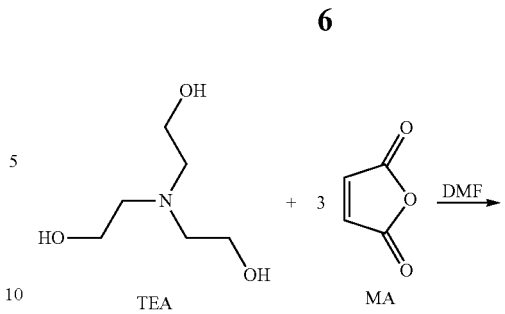

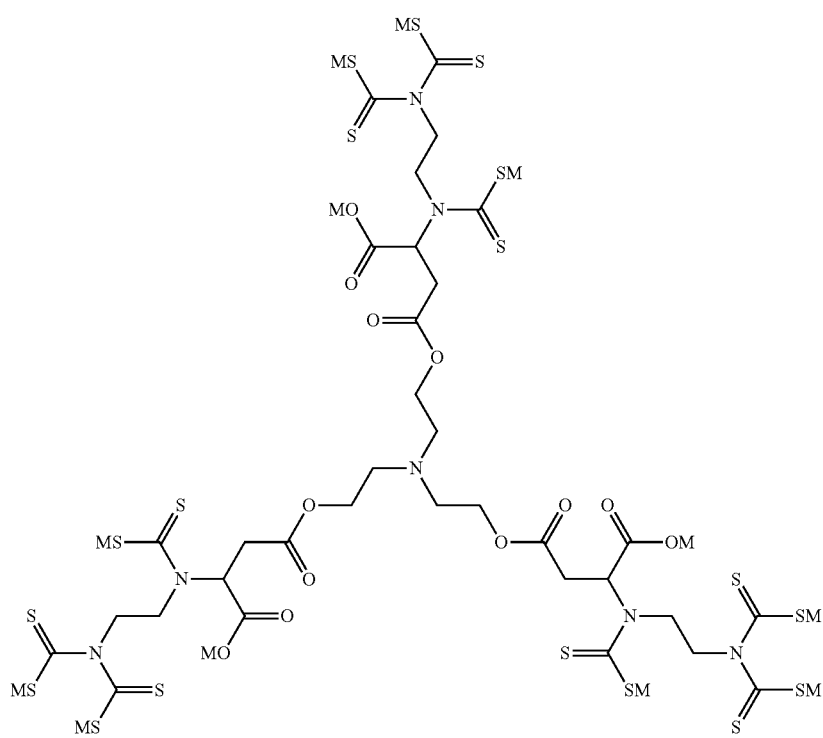

The present invention also provides a method for preparing a star-shaped hyperbranched polymer with a triethanolamine core, a carboxylate lateral group and a dithiocarboxylate end group, comprising steps of:

(1) adding maleic anhydride (MA for short) into a four-necked flask with a stirrer, a reflux condenser and a thermometer, then adding N,N-dimethylformamide (DMF for short), and stirring until the maleic anhydride dissolves; dropping a DMF solution of the triethanolamine (TEA for short) under nitrogen gas and a room temperature, and controlling a dropping speed for keeping a temperature lower than 25° C.; then stirring for 30 min, increasing the temperature to 80-90° C. and reacting for 5-10 h, for obtaining a star-shaped hyperbranched polymer of Triethanolamine/3Maleic anhydride (TEA/MA-3COOH for short); then cooling to 5-10° C., slowly dropping a MOH solution, wherein M is $Na^+$, $NH_4^+$ or $K^+$, and white solid is generated; suck-filtering and then washing twice with ethanol; drying under vacuum for obtaining a star-shaped hyperbranched polymer with a triethanolamine core and a maleate end group (TEA/MA-3COOM for short); wherein a reaction formula thereof is:

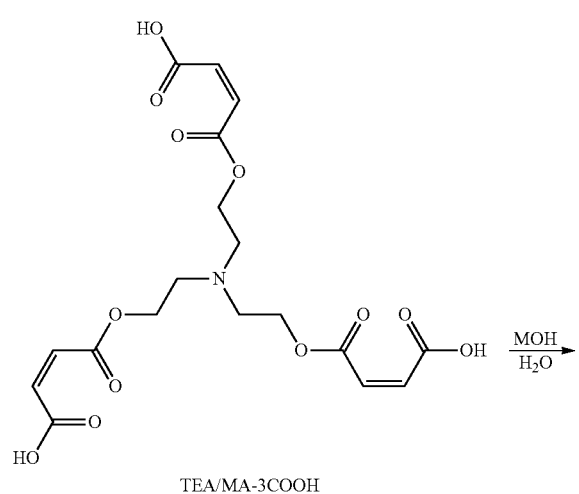

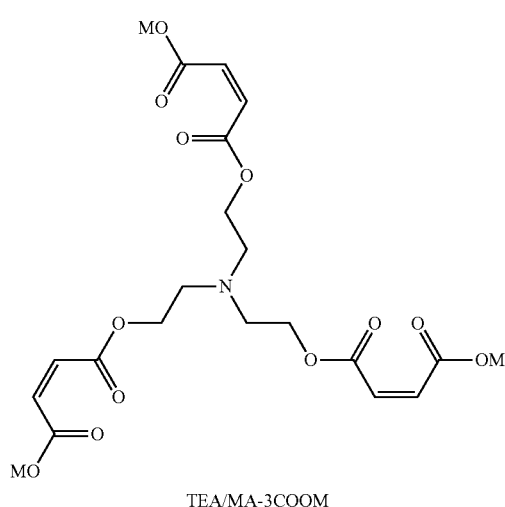

TEA/MA-3COOM (2) adding ethylenediamine (EDA for short) into a round flask with a stirrer, a reflux condenser and a thermometer, slowly dropping the MOH solution, wherein M is $Na^+$, $NH_4^+$ or $K^+$; controlling a dropping speed for keeping a temperature lower than 10° C.; then slowly dropping a water solution of the TEA/MA-3COOM, and controlling a dropping speed for keeping a temperature lower than 10° C.; then reacting for 20-24 h under nitrogen gas and a temperature of 80-90° C.; then vacuum suck-filtering at 80° C. for obtaining a star-shaped hyperbranched polymer of Triethanolamine/Maleic anhydride/Ethylenediamine (TME-3COOM for short); wherein a reaction formula thereof is:

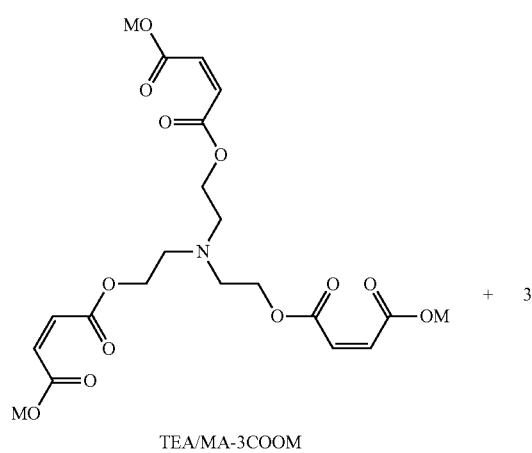

TEA/MA-3COOM

+ 3

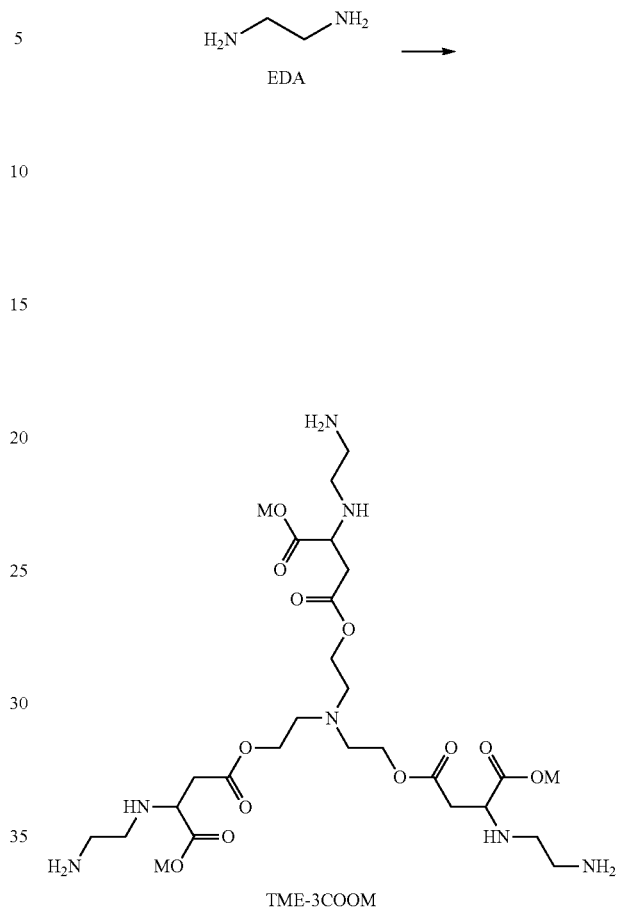

TME-3COOM (3) adding the TME-3COOM into a round flask with a stirrer, a reflux condenser and a thermometer, slowly dropping 20-50% alkali liquid, and controlling a dropping speed for keeping a reaction mixture temperature at 5-10° C.; dropping an alcoholic solution of carbon disulfide, and controlling a dropping speed for keeping a reaction mixture temperature at 5-10° C.; then reacting for 2-5 h at 5-10° C.; increasing a temperature to 25° C. and reacting for 3-5 h; storing the reacted mixture for a night, in such a manner that white deposit is separated out; filtering and washing with a small amount of alcohol, then filtering again for obtaining a target product: the star-shaped hyperbranched polymer with the triethanolamine core, the carboxylate lateral group and the dithiocarboxylate end group (TME-3COOM-9CSSM for short); wherein a reaction formula thereof is:

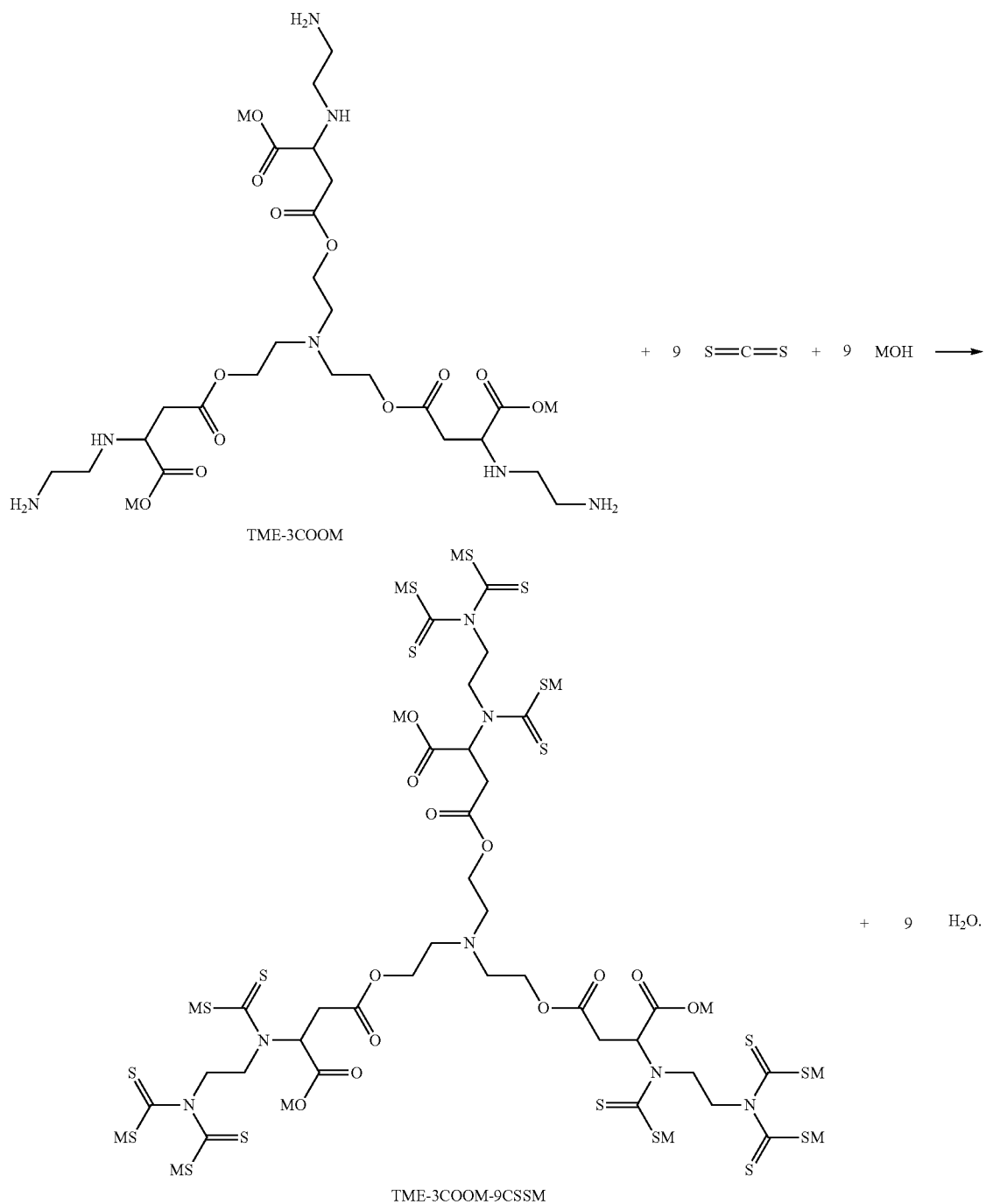

TME-3COOM

+ 9 S=C=S + 9 MOH ⟶

TME-3COOM-9CSSM

+ 9 H$_2$O.

According to the present invention, a mole ratio of the TEA, the MA, and sodium hydroxide is 1:(3.0-3.1):(3.0-3.1).

According to the present invention, a mole ration of the TEA/MA-3COOM, the EDA, and the alkali is 1:(4.0-6.0):(4.0-6.0).

According to the present invention, a mole ratio of the TME-3COOM, the carbon disulfide, and the alkali is 1:(11.25-13.50):(11.25-13.50).

According to the present invention, raw materials such as the TEA, the MA, the EDA, and the carbon disulfide are all commercially available.

According to the present invention, the alkali liquid is a water solution of sodium hydroxide, ammonia or potassium hydroxide, wherein sodium hydroxide, potassium hydroxide and ammonia are all commercially available.

According to the present invention, the alcohol is methanol, ethanol, propanol or butanol, which are all commercially available.

The star-shaped hyperbranched polymer prepared according to the present invention has the carboxylate lateral group, the dithiocarboxylate end group, and the triethanolamine core, which is a novel hyperbranched polymer. It is illustrated by experiments that the star-shaped hyperbranched polymer with a triethanolamine core, a carboxylate lateral group and a dithiocarboxylate end group is able to effectively stabilize heavy metals in fly ash due to a highly branched structure. Compared with conventional stabilizers which are widely used, the star-shaped hyperbranched polymer needs a low dosage, and stabilizes heavy metals while having a sufficient acid and alkali resistance.

The star-shaped hyperbranched polymer with a triethanolamine core, a carboxylate lateral group and a dithiocarboxylate end group according to the present invention not only is able to effectively stabilize heavy metals in fly ash, but also has a strong acid and alkali resistance. Therefore, the star-shaped hyperbranched polymer is able to be widely applied to MSWI fly ash treatment as well as treatment of waste water containing heavy metals.

BRIEF DESCRIPTION OF THE DRAWINGS

These and other objectives, features, and advantages of the present invention will become apparent from the accompanying drawings.

FIGS. 2-7 all illustrate toxicity testing results obtained by *method of solid waste leaching toxicity: acetate buffer solution method* (HJ/T300-2007), wherein nitric acid solutions with various pH values are used as leaching agents; wherein:

FIG. 2 illustrates effects of pH on As leaching toxicity.
FIG. 3 illustrates effects of pH on Cd leaching toxicity.
FIG. 4 illustrates effects of pH on Cr leaching toxicity.
FIG. 5 illustrates effects of pH on Ni leaching toxicity.
FIG. 6 illustrates effects of pH on Hg leaching toxicity.
FIG. 7 illustrates effects of pH on Pb leaching toxicity.

DETAILED DESCRIPTION OF THE PREFERRED EMBODIMENT

Figure 1:
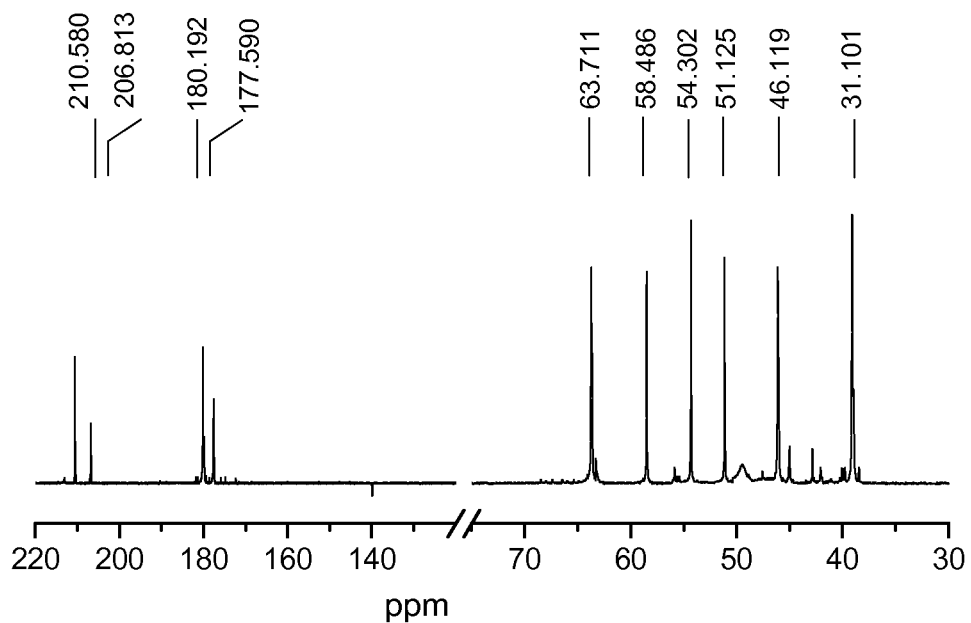
FIG. 1 is a carbon nuclear magnetic resonance spectrum of a star-shaped hyperbranched polymer prepared according to a first preferred embodiment.
Figure 2:
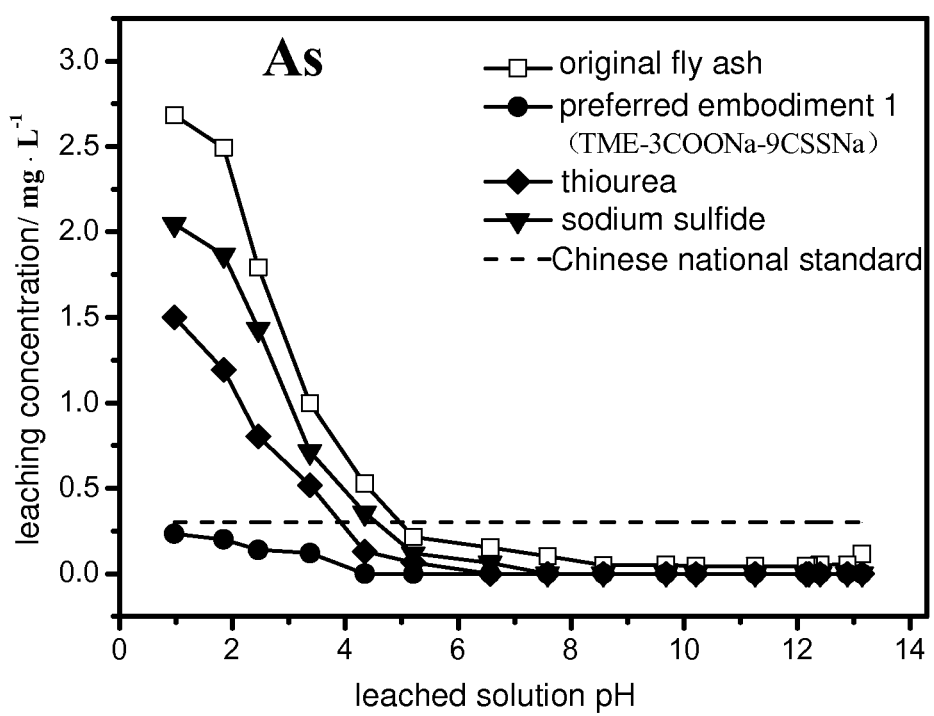
Figure 3:
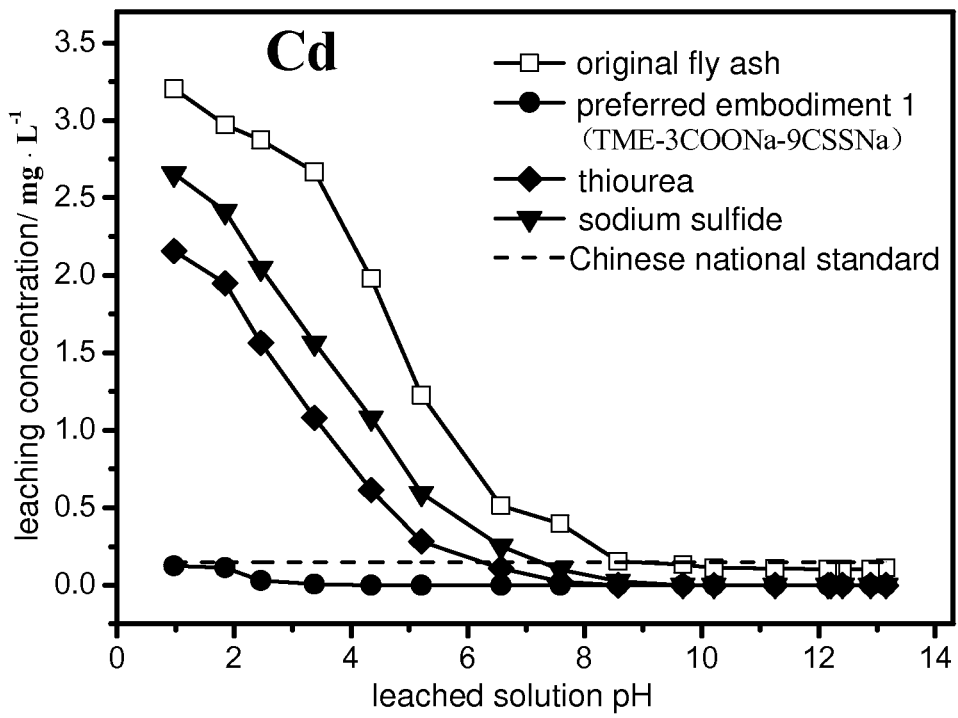
Figure 4:
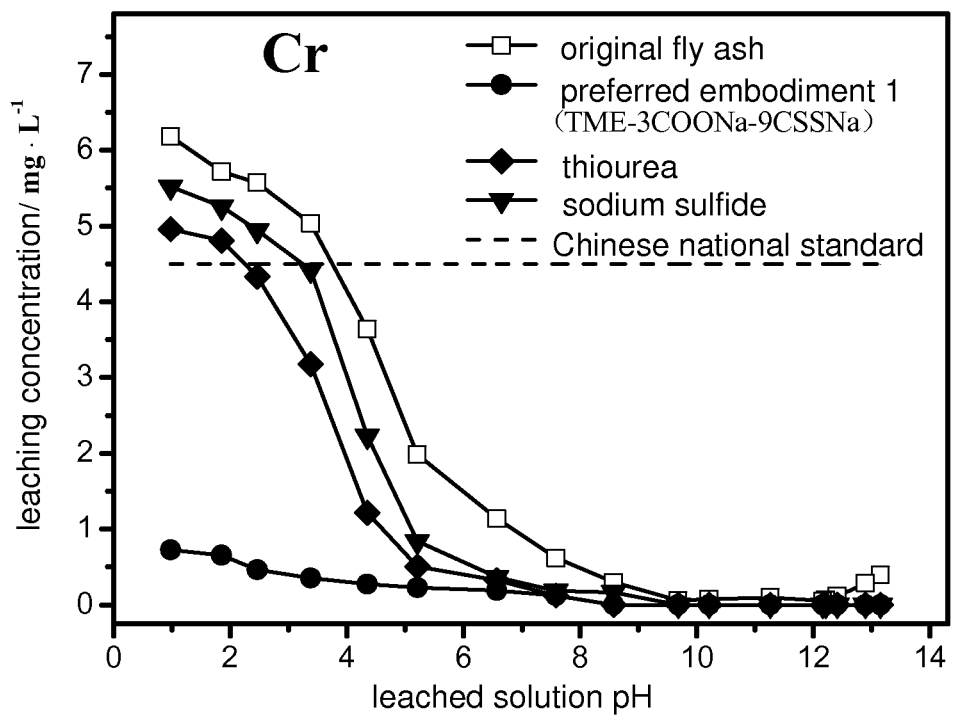
Figure 5:
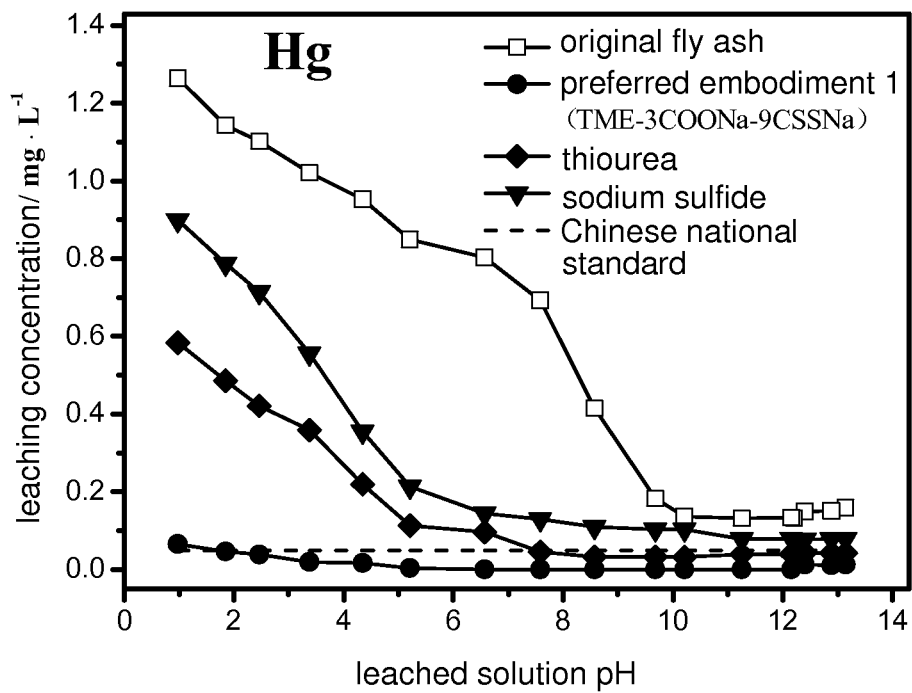
Figure 6:
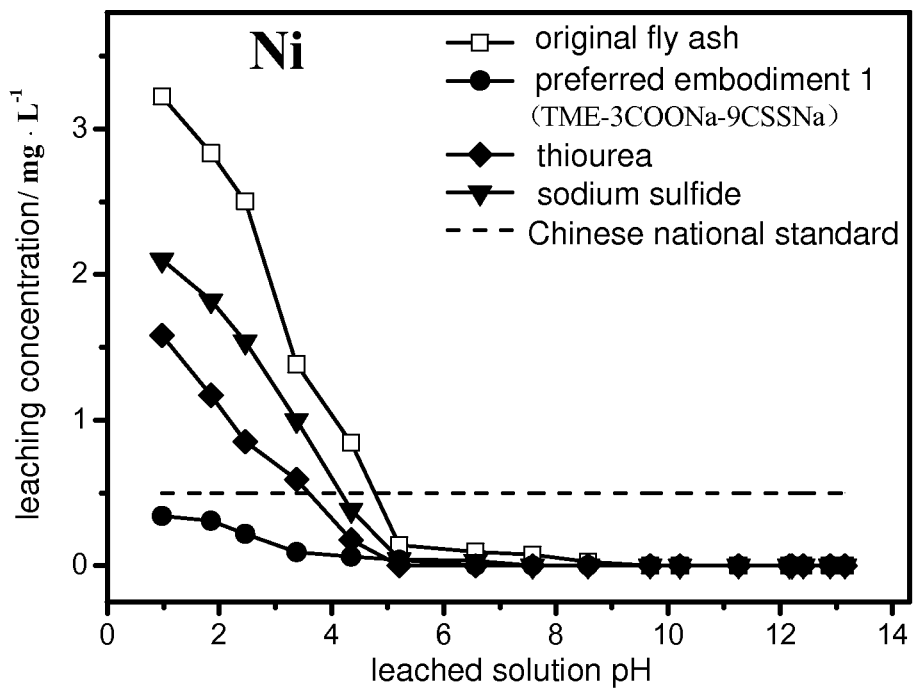
Figure 7:
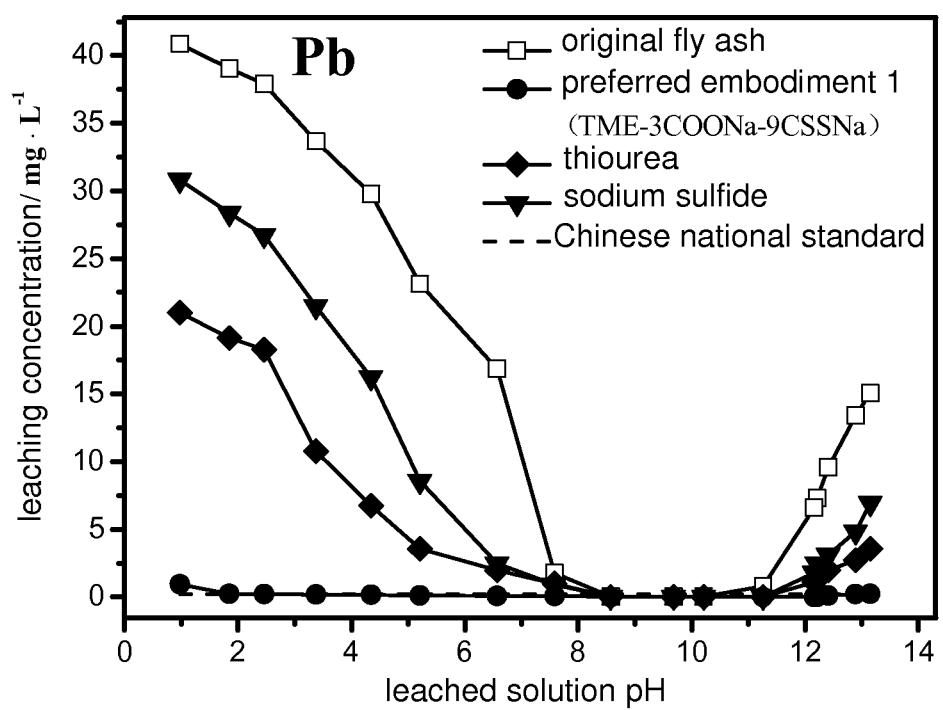

Referring to drawings and preferred embodiments, of the present invention is further illustrated. One skilled in the art will understand that the embodiment of the present invention as shown in the drawings and described above is exemplary only and not intended to be limiting. It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

Stabilizers in contrast examples 1-2 are all commercially available.

Contrast example 1: organic stabilizer thiourea ($H_2NCSNH_2$).

Contrast example 2: inorganic stabilizer sodium sulfide ($Na_2S$).

Preferred embodiment 1: preparation of a star-shaped hyperbranched polymer with a triethanolamine core, a sodium carboxylate lateral group and a sodium dithiocarboxylate end group (TME-3COONa-9CSSNa for short).

Adding 29.40 g (0.3 mol) MA into a four-necked flask with a stirrer, a reflux condenser and a thermometer, then adding 29.40 g DMF and stirring until the MA dissolves; inputting nitrogen gas and dropping 29.80 g (50%, 0.1 mol) DMF solution of TEA; controlling a dropping speed for keeping a temperature lower than 25° C.; then stirring for 30 min, increasing the temperature to 85° C. and reacting for 5 h, for obtaining TEA/MA-3COOH; then cooling to less than 10° C., slowly dropping 24.00 g (50%, 0.3 mol) NaOH solution, wherein white solid is generated; suck-filtering and then washing twice with ethanol; drying under vacuum for obtaining 50.84 g a star-shaped polymer with a triethanolamine core and a maleic acid sodium end group (TEA/MA-3COONa for short, and a yield thereof is 99.88%).

Adding 16.20 g (0.27 mol) EDA into a four-necked flask with a stirrer, a reflux condenser and a thermometer, slowly dropping 21.60 g (50%, 0.27 mol) NaOH solution; controlling a dropping speed for keeping a temperature lower than 10° C.; then slowly dropping 61.08 g (50%, 0.06 mol) water solution of the TEA/MA-3COONa, and controlling a dropping speed for keeping a temperature lower than 10° C.; then reacting for 20 h under nitrogen gas and a temperature of 80-90° C.; then vacuum-distilling at 80° C. for filtering out excess EDA and obtaining a star-shaped hyperbranched polymer with a triethanolamine core, a sodium carboxylate lateral group and an ethylenediamine end group (TME-3COONa for short); decreasing a temperature to less than 10° C.; slowly dropping 52.80 g (50.00%, 0.66 mol) NaOH solution, and controlling a dropping speed for keeping a reaction mixture temperature less than 10° C.; dropping 100.32 g (50.00%, 0.66 mol) ethanol solution of carbon disulfide, and controlling a dropping speed for keeping a reaction mixture temperature less than 10° C.; then reacting for 5 h at 10° C.; increasing a temperature to 25° C. and reacting for 5 h; storing the reacted mixture for a night, in such a manner that white deposit is separated out; filtering and washing with a small amount of ethanol, then filtering again for obtaining 91.23 g white product: the TME-3COONa-9CSSNa; wherein a yield thereof is 96.78%.

A $^{13}C$ nuclear magnetic resonance spectrum ($D_2O$) of the obtained star-shaped hyperbranched polymer is shown in FIG. 1, wherein absorbing peaks thereof are: δ39.101 ppm; 46.119 ppm; 51.125 ppm; 54.302 ppm; 58.486 ppm; 63.711 ppm; 177.590 ppm; 180.192 ppm; 206.813 ppm; and 210.580 ppm. Therefore, a formula thereof is: 
$N[CH_2CH_2OCOCH_2CH_2(COONa)N(CSSNa)CH_2CH_2N(CSSNa)_2]_3$.

Preferred embodiment 2: preparation of a star-shaped hyperbranched polymer with a triethanolamine core, an ammonium carboxylate lateral group and an ammonium dithiocarboxylate end group (TME-3COONH$_4$-9CSSNH$_4$ for short).

Adding 45.08 g (0.46 mol) MA into a four-necked flask with a stirrer, a reflux condenser and a thermometer, then adding 45.08 g DMF and stirring until the MA dissolves; inputting nitrogen gas and dropping 44.70 g (50%, 0.15 mol) DMF solution of TEA; controlling a dropping speed for keeping a temperature lower than 25° C.; then stirring for 30 min, increasing the temperature to 80° C. and reacting for 10 h, for obtaining TEA/MA-3COOH; then cooling to 10° C., slowly dropping 59.63 g (27%, 0.46 mol) ammonia, wherein white solid is generated; suck-filtering and then washing twice with ethanol; drying under vacuum for obtaining 73.38 g a star-shaped hyperbranched polymer with a triethanolamine core and a maleic acid ammonium end group (TEA/MA-3COONH$_4$ for short, a yield thereof is 99.03%) to be standby applied.

Adding 36.00 g (0.60 mol) EDA into a four-necked flask with a stirrer, a reflux condenser and a thermometer, slowly dropping 48.00 g (50%, 0.60 mol) NaOH solution; controlling a dropping speed for keeping a temperature lower than 10° C.; then slowly dropping 98.80 g (50%, 0.10 mol) water solution of the TEA/MA-3COONH$_4$, and controlling a dropping speed for keeping a temperature lower than 10° C.; then reacting for 24 h under nitrogen gas and a temperature of 80° C.; then vacuum-distilling at 80° C. for filtering out excess EDA and obtaining a star-shaped hyperbranched polymer with a triethanolamine core, an ammonium carboxylate lateral group and an ethylenediamine end group (TME-3COONH$_4$ for short).

Decreasing a temperature to less than 10° C.; slowly dropping 155.56 g (27.00%, 1.20 mol) NaOH solution, and controlling a dropping speed for keeping a reaction mixture temperature less than 10° C.; dropping 182.40 g (50.00%, 1.20 mol) ethanol solution of carbon disulfide, and controlling a dropping speed for keeping a reaction mixture temperature less than 10° C.; then reacting for 5 h at 10° C.; increasing a temperature to 25° C. and reacting for 5 h; storing the reacted mixture for a night, in such a manner that white deposit is separated out; filtering and washing with a small amount of ethanol, then filtering again for obtaining 147.89 g white product: the TME-3COONH$_4$-9CSSNH$_4$; wherein a yield thereof is 97.06%.

A nuclear magnetic resonance spectrum of the obtained star-shaped hyperbranched polymer is: $^{13}$C NMR (D$_2$O): δ38.986 ppm; 46.125 ppm; 51.478 ppm; 54.936 ppm; 58.176 ppm; 63.96 ppm; 177.213 ppm; 181.083 ppm; 205.349 ppm; and 213.142 ppm. Therefore, a formula thereof is: N[CH$_2$CH$_2$OCOCH$_2$CH$_2$(COONH$_4$)N(CSSNH$_4$)CH$_2$CH$_2$N(CSSNH$_4$)$_2$]$_3$.

Preferred embodiment 3: stabilizing treatment of MSWI fly ash.

The fly ash is from a waste incineration site. Leaching toxicity testing uses acetate defined in *method of solid waste leaching toxicity: acetate buffer solution method* (HJ/T300-2007). A pollution control standard is *Landfill Pollution Control Standard* (GB16889-2008). Results are shown in Table 1. It is illustrated that leaching concentrations of Pb and Hg in fly ash are high, and are over the standard. Other heavy metal elements are within the standard.

TABLE 1 heavy metal leaching toxicity of original fly ash/mg · L$^{-1}$

| content | As | Cd | Cr | Cu | Hg | Ni | Pb | Zn |
|---|---|---|---|---|---|---|---|---|
| leaching toxicity | 0.022 | 0.101 | 0.012 | 0.139 | 0.149 | 0 | 9.983 | 0.145 |
| standard limit | 0.3 | 0.15 | 4.5 | 40 | 0.05 | 0.5 | 0.25 | 100 |

TABLE 2 heavy metal leaching toxicity of fly ash stabilized production

| No. | stabilizer | concentration (%) | Pb leaching concentration (mg · L$^{-1}$) | Hg leaching concentration (mg · L$^{-1}$) |
|---|---|---|---|---|
| original fly ash | — | — | 9.983 | 0.149 |
| preferred embodiment 1 | TME-3COONa-9CSSNa | 0.5% | 2.034 | 0.104 |
| | | 1.0% | 1.205 | 0.078 |
| | | 2.5% | 0.015 | 0.021 |
| | | 5.0% | 0 | 0.002 |
| preferred embodiment 2 | TME-3COONH$_4$-9CSSNH$_4$ | 0.5% | 2.001 | 0.111 |
| | | 1.0% | 1.291 | 0.092 |
| | | 2.5% | 0.019 | 0.029 |
| | | 5.0% | 0 | 0.001 |
| contrast example 1 | thiourea | 0.5% | 6.432 | 0.124 |
| | | 1.0% | 4.349 | 0.114 |
| | | 2.5% | 3.527 | 0.087 |
| | | 5.0% | 1.983 | 0.043 |
| | | 7.5% | 1.037 | 0.017 |
| | | 10% | 0 | 0 |
| contrast example 2 | sodium sulfide | 0.5% | 7.192 | 0.132 |
| | | 1.0% | 5.238 | 0.128 |
| | | 2.5% | 4.423 | 0.103 |
| | | 5.0% | 3.128 | 0.078 |
| | | 7.5% | 1.832 | 0.032 |
| | | 10% | 0.642 | 0.022 |
| standard limit | | | 0.25 | 0.05 |

The fly ash of waste is stabilized with the TME-3COOM-9CSSM prepared in the preferred embodiments 1-2, H$_2$NCSNH$_2$ in contrast example 1, and Na$_2$S in contrast example 2. A method of stabilizing fly ash using the TME-3COOM-9CSSM, H$_2$NCSNH$_2$ and Na$_2$S comprises steps of: dissolving a certain amount of the stabilizer in 40 ml deionized water, thoroughly stirring before adding 100 g incinerated fly ash, and stirring for 30 min for forming a thick compound; then drying with natural ventilation for obtaining the stabilized production of the incinerated fly ash.

Leaching toxicity testing is provided according to *method of solid waste leaching toxicity: acetate buffer solution method* (HJ/T300-2007). A pollution control standard thereof is *Landfill Pollution Control Standard* (GB16889-2008). Results are shown in Table 2.

Referring to Table 2, the TME-3COOM-9CSSM according to the present invention has a very good stabilizing effect on the incinerated fly ash. When a dosage thereof is 0.5% of fly ash weight, the Pb and Hg leaching concentrations in the fly ash stabilized by the TME-3COOM-9CSSM are significantly reduced; when the dosage is 2.5% of fly ash weight, the Pb and Hg leaching concentrations in the fly ash stabilized are lower than a limit of the *Landfill Pollution Control Standard*.

Referring to contrast example 1, when a dosage of thiourea is 10% of fly ash weight, the Pb and Hg leaching concentrations in the fly ash stabilized are lower than the limit of the *Landfill Pollution Control Standard*. Referring to contrast example 2, when a dosage of sodium sulfide is 10% of fly ash weight, the Hg leaching concentration in the fly ash stabilized is lower than the limit of the *Landfill Pollution Control Standard* (GB16889-2008), but the one of Pb is higher than the limit.

Therefore, the TME-3COOM-9CSSM according to the present invention is significantly better than the conventional thiourea and sodium sulfide fly ash stabilizers.

Preferred embodiment 4: acid resistance testing of fly ash stabilized.

Leaching toxicity testing is provided on original fly ash and fly ash stabilized by stabilizer with a dosage of 5% of fly ash weight with *method of solid waste leaching toxicity: acetate buffer solution method* (HJ/T300-2007), wherein nitric acid solutions with various pH values are used as leaching agents. Results thereof are shown in FIGS. 2-7.

Because results of TME-3COOM-9CSSM prepared in preferred embodiments 1-2 are similar, only the results of TME-3COONa-9CSSNa in preferred embodiment 1 are shown in FIGS. 2-7, wherein pH refers to leached solution pH instead of leaching agent pH for better describing the acid and alkali resistance of the present invention.

Judging from the results, the fly ash stabilized by the TME-3COONa-9CSSNa has sufficient acid and alkali resistance. When leached solution pH is 0.98-6.57 (which means leaching with an acid solution whose pH is −0.225-0), leaching concentrations of As, Cd, Cr and Ni are extremely low and lower than the limit of *Landfill Pollution Control Standard* (GB16889-2008). When leached solution pH is 1.85-6.57 (which means leaching with an acid solution whose pH is −0.170-0), leaching concentrations of Hg and Pb are lower than the limit of *Landfill Pollution Control Standard* (GB16889-2008). Only when leached solution pH is lower than 1.85 (which means leaching with an acid solution whose pH is lower than −0.170), leaching concentrations of Hg and Pb are over the limit. When leached solution pH is more than 12.40 (which means leaching with a NaOH solution), leaching concentrations of Pb is extremely low and is lower than the limit of *Landfill Pollution Control Standard* (GB16889-2008). However, the conventional thiourea and sodium sulfide fly ash stabilizers have poor acid and alkali resistance.

Therefore, the TME-3COOM-9CSSM according to the present invention has sufficient acid and alkali resistance.

What is claimed is:

1. A star-shaped hyperbranched polymer with a triethanolamine core, a carboxylate lateral group and a dithiocarboxylate end group, wherein a formula thereof is: N[CH$_2$CH$_2$OCOCH$_2$CH$_2$(COOM)N(CSSM)CH$_2$CH$_2$N(CSSM)$_2$]$_3$, wherein M is Na$^+$, NH$_4^+$ or K$^+$; a structural formula thereof is:

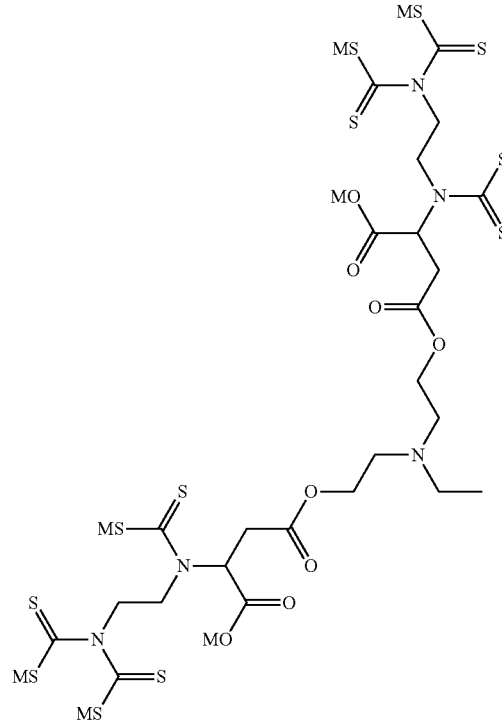

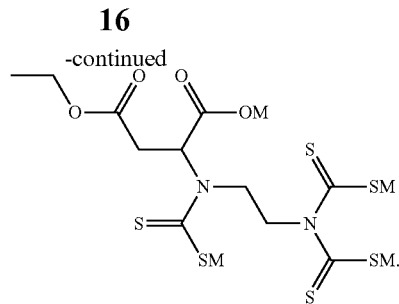

2. A method for preparing the star-shaped hyperbranched polymer as recited in claim 1, wherein raw material of the star-shaped hyperbranched polymer comprises triethanolamine, maleic anhydride, ethylenediamine, carbon disulfide and alkali; the method comprises steps of:

(1) adding the maleic anhydride (MA for short) into a four-necked flask with a stirrer, a reflux condenser and a thermometer, then adding N,N-dimethylformamide (DMF for short) and stirring until the maleic anhydride dissolves; dropping a DMF solution of the triethanolamine (TEA for short) under nitrogen gas and a room temperature, and controlling a dropping speed for keeping a temperature lower than 25° C.; then stirring for 30 min, increasing the temperature to 80-90° C. and reacting for 5-10 h, for obtaining a star-shaped hyperbranched polymer of Triethanolamine/3Maleic anhydride (TEA/MA-3COOH for short); then cooling to 5-10° C., slowly dropping a MOH solution (\wherein M is Na$^+$, NH$_4^+$ or K$^+$), and white solid is generated; suck-filtering and then washing twice with ethanol; drying under vacuum for obtaining a star-shaped hyperbranched polymer with a triethanolamine core and a maleate end group (TEA/MA-3COOM for short); wherein a reaction formula thereof is:

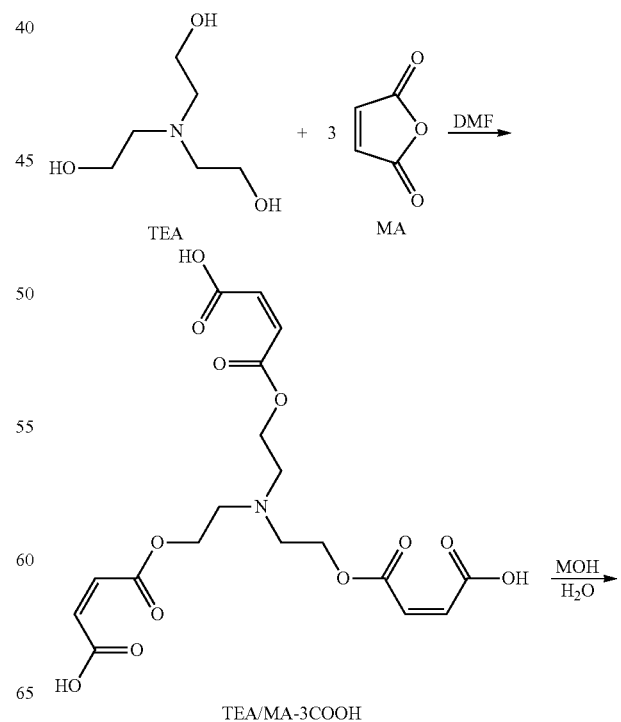

TEA/MA-3COOH

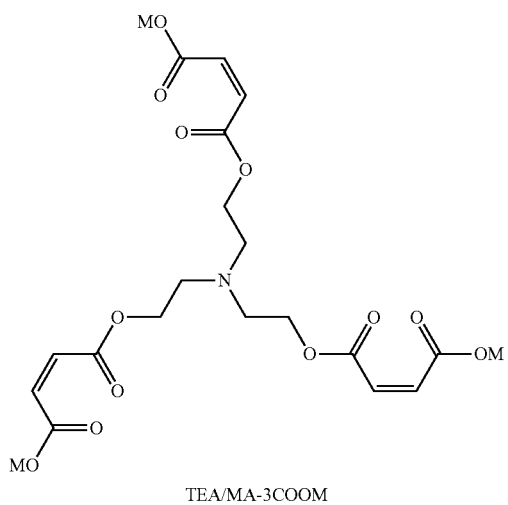

TEA/MA-3COOM (2) adding the ethylenediamine (EDA for short) into a round flask with a stirrer, a reflux condenser and a thermometer, slowly dropping the MOH solution (wherein M is $Na^+$, $NH_4^+$ or $K^+$); controlling a dropping speed for keeping a temperature lower than 10° C.; then slowly dropping a water solution of the TEA/MA-3COOM, and controlling a dropping speed for keeping a temperature lower than 10° C.; then reacting for 20-24 h under nitrogen gas and a temperature of 80-90° C.; then vacuum suck-filtering at 80° C. for obtaining a star-shaped hyperbranched polymer of Triethanolamine/Maleic anhydride/Ethylenediamine (TME-3COOM for short); wherein a reaction formula thereof is:

TEA/MA-3COOM + 3 EDA →

TME-3COOM and (3) adding the TME-3COOM into a round flask with a stirrer, a reflux condenser and a thermometer, slowly dropping 20-50% alkali liquid, and controlling a dropping speed for keeping a reaction mixture temperature at 5-10° C.; dropping an alcoholic solution of carbon disulfide, and controlling a dropping speed for keeping a reaction mixture temperature at 5-10° C.; then reacting for 2-5 h at 5-10° C.; increasing a temperature to 25° C. and reacting for 3-5 h; storing the reacted mixture for a night, in such a manner that white deposit is separated out; filtering and washing with a small amount of alcohol, then filtering again for obtaining a target product: the star-shaped hyperbranched polymer with the triethanolamine core, the carboxylate lateral group and the dithiocarboxylate end group (TME-3COOM-9CSSM for short); wherein a reaction formula thereof is:

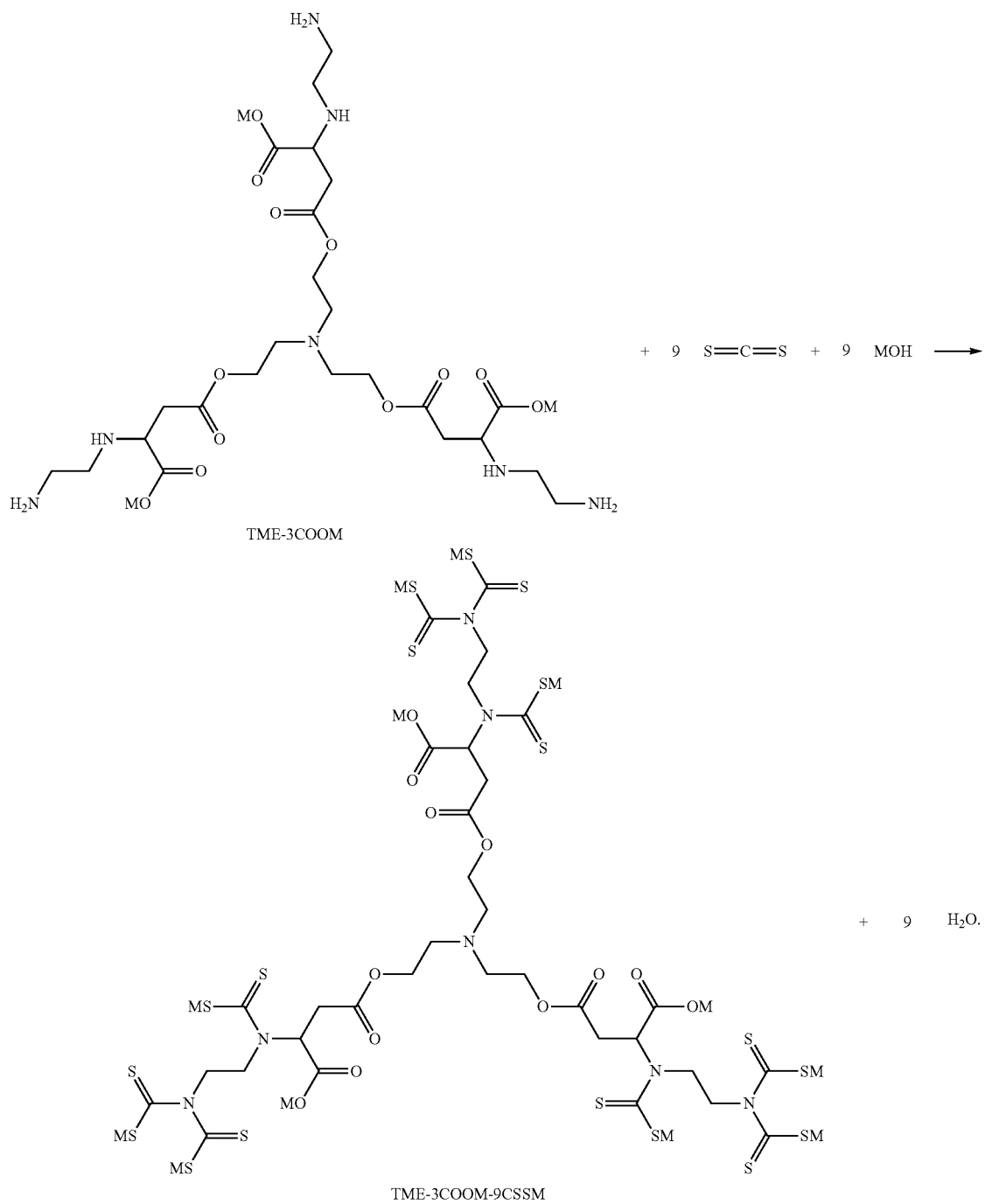

3. The method, as recited in claim 2, wherein a mole ratio of the TEA, the MA, and the alkali is 1:(3.0-3.1):(3.0-3.1); a mole ration of the TEA/MA-3COOM, the EDA, and the alkali is 1:(4.0-6.0):(4.0-6.0); a mole ratio of the TME-3COOM, the carbon disulfide, and the alkali is 1:(11.25-13.50):(11.25-13.50).

4. The method, as recited in claim 2, wherein the alcohol is methanol, ethanol, propanol or butanol; the alkali liquid is a water solution of ammonia, sodium hydroxide or potassium hydroxide.

5. A method for stabilizing incinerated fly ash of waste, comprising applying the star-shaped hyperbranched polymer as recited in claim 1.

6. The method, as recited in claim 5, specifically comprising steps of:
preparing a water solution of TME-3COOM-9CSSM as a stabilizer, then dissolving the stabilizer in water and adding to the incinerated fly ash, wherein a dosage thereof is 0.5-5% of a fly ash weight; keeping stirring for 15-30 min, then drying with natural ventilation for obtaining a stabilized product of the incinerated fly ash.

* * * * *